United States Patent [19]

Aoki

[11] Patent Number: 4,826,810

[45] Date of Patent: May 2, 1989

[54] SYSTEM AND METHOD FOR TREATING ANIMAL BODY TISSUES TO IMPROVE THE DIETARY FUEL PROCESSING CAPABILITIES THEREOF

[76] Inventor: Thomas T. Aoki, 1021 El Sur Way, Sacramento, Calif. 95825

[21] Appl. No.: 27,852

[22] Filed: Mar. 19, 1987

Related U.S. Application Data

[63] Continuation of Ser. No. 678,511, Dec. 10, 1984, abandoned, and a continuation-in-part of Ser. No. 562,435, Dec. 6, 1983, abandoned.

[51] Int. Cl.$^4$ .............................................. A61K 37/26
[52] U.S. Cl. ........................................ 514/3; 604/151
[58] Field of Search ............................................ 514/3

[56] References Cited

U.S. PATENT DOCUMENTS

| | | | |
|---|---|---|---|
| 3,512,517 | 5/1970 | Kadish et al. | 128/2 |
| 3,837,339 | 9/1974 | Aisenberg et al. | 128/213 |
| 4,055,175 | 10/1977 | Clemens et al. | 128/213 |
| 4,073,292 | 2/1978 | Edelman | 128/214 E |
| 4,077,405 | 3/1978 | Haerten et al. | 128/214 F |
| 4,151,845 | 5/1979 | Clemens | 128/214 E |
| 4,206,755 | 6/1980 | Klein | 128/214 E |
| 4,245,634 | 1/1981 | Albisser et al. | 128/213 R |
| 4,253,456 | 3/1981 | Schindler et al. | 128/214 R |
| 4,275,727 | 6/1981 | Keeri-Szanto | 128/214 E |
| 4,280,494 | 7/1981 | Cosgrove et al. | 128/213 R |
| 4,282,872 | 8/1981 | Franetzki et al. | 128/212 R |
| 4,340,458 | 7/1982 | Lerner et al. | 204/195 R |
| 4,366,033 | 12/1982 | Richter et al. | 204/1 T |

OTHER PUBLICATIONS

*Chemical Abstracts*, vol. 92 13534m.
*Chemical Abstracts*, vol. 89 39926u (1978).
*Diabetes*, 31 (1) 46 (1/82).
*J. Clin Invest.*, Hi837 (4/83).
"New Joslin Findings on Control", Dr. Aoki Directs Unique Study, Joslin Diabetes Center Newsletter, Fall 1982, p. 1.

*Primary Examiner*—Frederick E. Waddell
*Attorney, Agent, or Firm*—Townsend and Townsend

[57] ABSTRACT

A system and method for treating an animal subject having predetermined body tissues characterized by abnormal or impaired dietary fuel processing capabilities. A dietary fuel of preselected type and quantity is administered to the subject to produce in the blood supply to these body tissues a substantially elevated carbohydrate concentration during a time period following such administration. During at least a portion of the time period of such elevated carbohydrate concentration, insulin is injected into the subject in accordance with a prearranged insulin concentration versus time function. This function is independent of the magnitude of the carbohydrate concentration in the blood stream, i.e. the carbohydrate concentration does not have to be measured since it is not used to control the insulin injection. The insulin injection function produces a rapid increase in the free insulin concentration in the blood supply to the involved body tissues and is preferably a prearranged series of spaced insulin pulses that produce a series of peaks in the free insulin concentration in the blood supply to the target tissues and a continuously rising interpeak value of free insulin concentration. The coincidence of the elevated carbohydrate concentration and rapid increase in free insulin concentration thereby produces a functional improvement in the dietary fuel processing capabilities of the involved body tissues. A computer controlled insulin pumping system functions under program control to provide the series of insulin pulses.

21 Claims, 2 Drawing Sheets

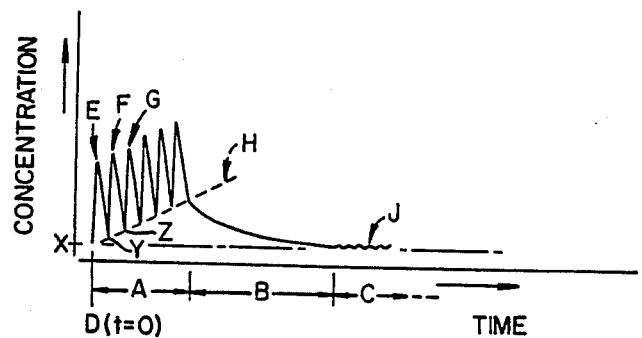
FIG._1.
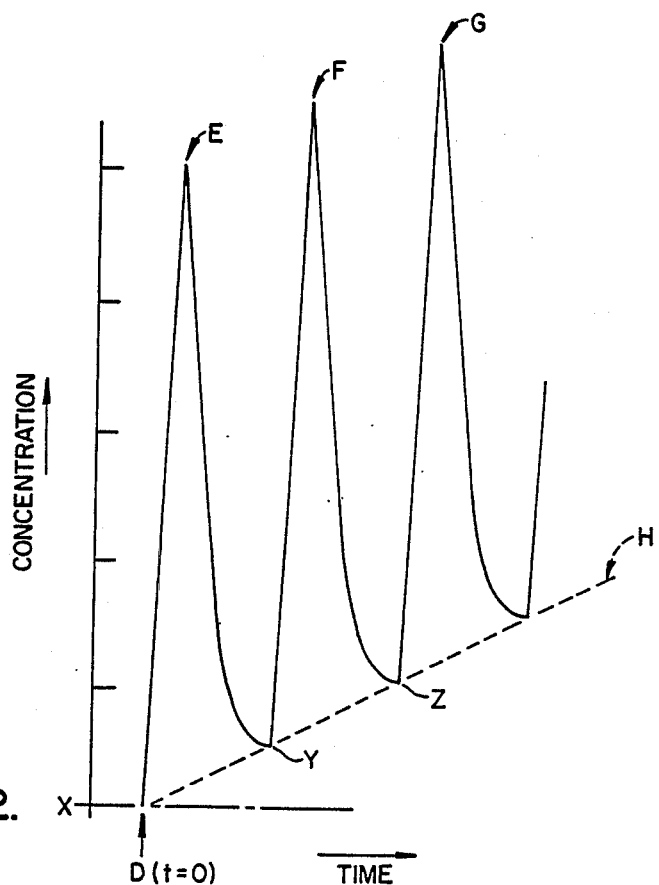
FIG._2.
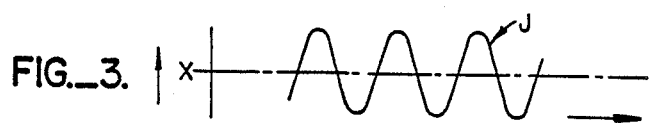
FIG._3.

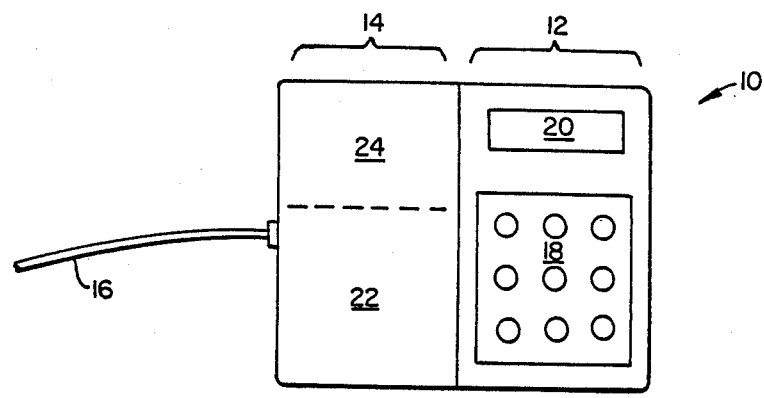
FIG._4.
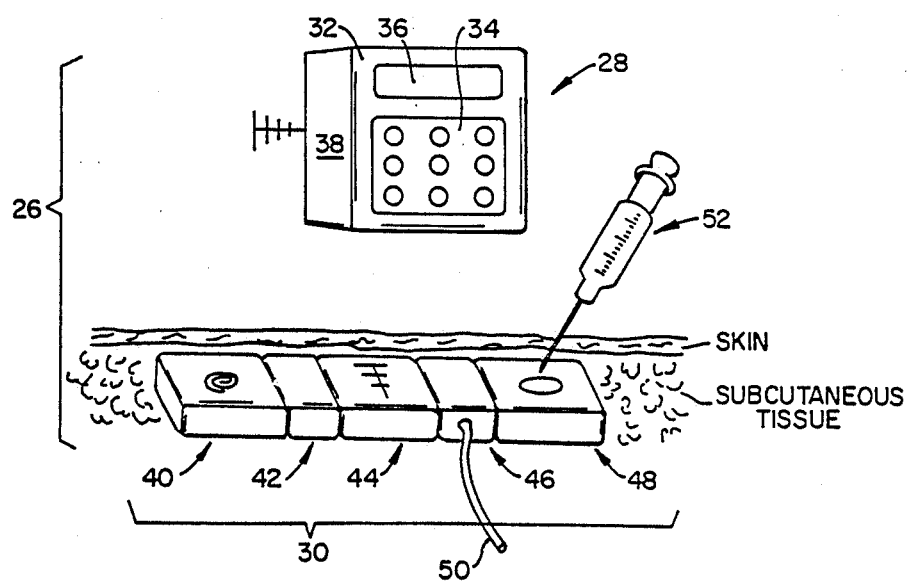
FIG._5.

100
SYSTEM AND METHOD FOR TREATING ANIMAL BODY TISSUES TO IMPROVE THE DIETARY FUEL PROCESSING CAPABILITIES THEREOF

RELATED APPLICATION

This application is continuation of U.S. application Ser. No. 678,511, filed Dec. 10, 1984, now abandoned, which is a continuation-in-part of U.S. application Ser. No. 562,435, filed Dec. 6, 1983, and now abandoned.

BACKGROUND OF THE INVENTION

This invention relates to timing the administration of insulin and various fuels (carbohydrates, proteins, and fats) to individuals whose fuel processing (i.e., oxidation, storage, and conversion to other substrates) capabilities are chronically abnormal (e.g., diabetic subjects) or acutely disrupted (e.g., accidentally or surgically traumatized patients).

The normal fuel processing capabilities of the body, such as of the liver and other tissues, e.g., muscle, can be disrupted by disease (e.g., diabetes) and by trauma (accidental or surgical).

(Insulin is often administered in large quantities to diabetic subjects, surgical patients or accident (especially burn) victims in attempts to restore normal fuel processing capabilities and to prevent the breakdown of muscle protein. Since massive doses of insulin lower blood sugar levels, glucose may also be infused.

Established treatment programs for diabetic patients administre insulin to control blood glucose concentrations. Insulin infusion patterns based directly on measured blood glucose levels are disclosed in Aisenberg et al., U.S. Pat. No. 3,387,339; Klein, U.S. Pat. No. 4,206,755; Edelman, U.S. Pat. No. 4,073,292; and Chem. Abstracts, 92:135345m. Insulin infusion patterns based on projected blood glucose levels and expected changes in blood glucose levels, calculated using measured blood glucose levels, are disclosed in Ablisser et al., U.S. Pat. No. 4,245,634; Schindler et al, U.S. Pat. No. 4,253,456; Clemens, U.S. Pat. No. 4,151,845; Clemens et al, U.S. Pat. No. 4,055,175; and Chem. Abstracts, 89:39926u. In programs of the above types, both the amount of insulin infused and the duration of the infusion are dependent on measured glucose concentrations. That is, when measured glucose concentration and/or projected concentrations arise to a certain perscribed limit, insulin is administered. Insulin infusion then continues until such glucose concentrations approach or fall below a certain level.

In addition to these patterns of insulin infusion based on concurrently-measured glucose levels, insulin-administering devices have been developed which can infuse insulin according to a predetermined profile of the patient's insulin requirements. For example, Franetzki et al, U.S. Pat. No. 4,482,872, discloses such a device wherein a base rate of insulin is continuously infused and the predetermined program (stored in a microprocessor), which typically administers a larger amount (pulse) of insulin, can be called up by the patient when needed. Haerten et al, U.S. Pat. No. 4,077,405, likewise discloses a device which can administer pulses of medication (e.g., insulin) over a constant baseline in response to pre-programmed or manually-controlled signals. These devices administer insulin in patterns which, like the above-mentioned methods which respond to concurrently-measured glucose concentrations, are a function of and are designed to directly control the actual concentration of glucose in the blood stream.

SUMMARY OF THE INVENTION

In general, the invention features a method of treating a diabetic or a traumatized subject which includes the steps of (1) establishing an elevated carbohydrate concentration in the subject's metabolic system and (2) activating the dietary carbohydrate processing capabilities of the subject's liver by administering insulin to increase the "free" insulin concentration in said subject's metabolic system during at least part of the period when the carbohydrate concentration is elevated, with said insulin being administered in pulses to produce a series of peaks in said "free" insulin concentration.

In preferred embodiments the changes in the free insulin concentration are effected by administering time-varying quantities of insulin, the elevated carbohydrate concentration is established by the ingestion or infusion of carbohydrates, the administering step is initiated coincident with the establishing step, the insulin is administered in pulses, a primary series of insulin pulses which produces sharp peaks over a gradually increasing interpeak concentration is followed by an interval during which no insulin is administered to allow the insulin concentration to return to that concentration which existed prior to the administration of the primary series of pulses (the baseline concentration), the interval is followed by the administration of a secondary series of insulin pulses to produce an insulin concentration which oscillates about the baseline concentration which maintains the fuel processing system in an active state, the average amount of insulin in the pulses of the secondary series is less than the average amount of insulin in the pulses of the primary series, and the secondary series continues during the entire period between carbohydrate ingestions or infusions.

Further in preferred embodiments the time-varying quantities of insulin are administered using an external or implantable programmable insulin infusion pump.

The program of changes in insulin concentrations of the present invention activates and maintains processing capabilities for body fuels such as carbohydrates (glucose, fructose, sucrose, galactose, starches, and related analogs and derivatives), amino acids, and lipids of a diabetic or a traumatized patient's system. In diabetic patients, the method of insulin administration indirectly controls blood glucose concentrations by addressing the underlying problem of diabetes, namely the absence of autoregulation of glucose concentrations by the metabolic system, by rapidly and efficiently activating and maintaining the metabolically-dormant dietary carbohydrate processing system, in particular the liver but including muscle.

Other features and advantages of the invention will be apparent from the following description of the preferred embodiment thereof, and from the claims.

DESCRIPTION OF THE PREFERRED EMBODIMENT

We first briefly describing the drawings.

DRAWINGS

FIG. 1 shows the concentration of "free" insulin achieved by the preferred embodiments of the invention.

FIG. 2 is an enlargement of Section A of FIG. 1.

FIG. 3 is an enlargement of Section C of FIG. 1.

FIG. 4 is a schematic block diagram of an external programmable insulin pump programmed to deliver insulin according to the present invention.

FIG. 5 is a schematic block diagram of an implantable programmable insulin pump programmed to deliver insulin according to the present invention.

DESCRIPTION

The present program of insulin concentration changes is directed to coordinating elevated carbohydrate concentrations in body tissues, for example due to the ingestion of a carbohydrate-containing meal or due to a carbobohydrate (e.g., glucose) infusion, with the insulin concentrations resulting from the program so that they may act together to activate and maintain the body's fuel processing capabilities. In particular, the program is designed to coordinate elevated liver and portal vein glucose concentrations with the aforementioned insulin concentrations so as to achieve the dietary carbohydrate processing system which, based on investigations into the enzymes involved in the metabolism of glucose and the distribution of exogenous and endogenous glucose in the metabolic system, is believed to be primarily in the liver and to a lesser extent in muscle. Both the amount of insulin infused and the duration of the administration of the insulin pulses are independent of prevailing blood glucose levels.

Due to the binding of insulin to antibodies in persons who has received insulin (e.g., insulin-taking diabetic subject), the concentration of insulin which is available to interact so as to require fuel processing capabilities, in particular to regulate blood glucose concentrations, is typically much lower than the total concentration of insulin in the system. The concentration of insulin which is so available is referred to as the "free" insulin concentration.

The initial portion of the program is designed to activate the body's fuel processing capabilities, in particular the dietary carbohydrates processing system. In order to activate the system, the body's tissues, in particular the liver (but including muscle), must see (i.e., be subject to) sharp changes in the "free" insulin concentration as well as a gradual overall increase in the interpeak "free" insulin concentration, at the same time that the concentration of glucose in the liver and portal vein is high, e.g., after ingestion of a carbohydrate-containing meal or after an infusion of carbohydrates. Section A of FIG. 1 and FIG. 2 show the necessary pattern of "free" insulin concentrations. The combination of these three factors, i.e., rapid changes in "free" insulin concentration superimposed over a gradually increasing "free" insulin concentration in the presence of a high intra-liver or portal vein glucose concentration, will cause the liver (and to a lesser extent muscle) to synthesize and activate the enzymes responsible for metabolizing glucose.

After the system is activated, it may be maintained by administering time-varying quantities of insulin to produce a "free" insulin concentration which oscillates near or about the baseline concentration, i.e., that concentration of insulin which existed prior to administering the initial portion of the program. Section C of FIG. 1 and FIG. 3 show the oscillating "free" insulin concentrations.

The time-varying quantities of insulin are preferably pulses of insulin, i.e., injections or infusions which start and stop within a short period of time (on the order of seconds). However, any time-varying quantities which produce the necessary pattern of "free" insulin concentration may be used.

The administration of a primary series of pulses of insulin spaced closely enough such that the effect of one pulse (i.e., a "free" insulin concentration peak) has not been completely dissipated before the next pulse is administered will result in the necessary sharp changes in "free" insulin concentration over an increasing interpeak insulin concentration. Referring to FIGS. 1 and 2, a carbohydrate-containing meal is ingested or a carbohydrate infusion is initiated at D, or time =0, when the "free" insulin concentration is X. X represents the concentration of "free" insulin present in the patient's system prior to the administration of the insulin pulses of the primary series, and is herein referred to as the baseline concentration. For example, in a diabetic patient X would be the lowest "free" insulin concentration in the patient's system following the last insulin injection of a typical treatment program. Typical baseline "free" insulin concentrations are from 5 to 15 micro-Units of insulin per milliliter of serum ($\mu$U/ml).

Coincident with or shortly following the establishment of an elevated carbohydrate concentration, the first pulse of the primary series of the present insulin delivery program is administered, which will result in peak E. The pulse is an amount of insulin sufficient to cause the peak "free" insulin concentration in the blood to reach from 50 to 3000 $\mu$U/ml, preferably 100 to 2000 $\mu$U/ml. When the "free" insulin concentration decreases by about 90% to Y (i.e., to about 10% over the "free" insulin concentration at the time of administering the first pulse) the second pulse of the primary series is administered, which will result in peak F. When the "free" insulin concentration again decreases by about 90% to Z, or to about 10% over the "free" insulin concentration at the time of administering the second pulse, the next pulse of the primary series is administrated, which will result in peak G. Repetition of this process will result in the increasing interpeak "free" insulin concentration denoted by line H. In the primary series of insulin pulses the amount of insulin injecter per pulse may be constant or may vary provided the peak "free" insulin concentration achieved after each pulse is from 50 to 3000 $\mu$U/ml, preferably 100 to 2000 $\mu$U/ml. The interpulse duration also may be constant or may vary, provided the next subsequent pulse is administered before the insulin concentration resulting from the previous pulse has returned to that concentration which existed prior to administering the previous pulse, so that the interpeak "free" insulin concentration increases by 10 to 500 $\mu$U/ml from one pulse to the next. The duration of the primary series administered with each meal or carbohydrate infusion does not exceed three hours and generally falls within the range of about 6 to 180 minutes. Particularly effective results have been obtained with a series of 10 pulses, administered six minutes apart, over an interval of 56 minutes. Since it is desirable to administer the least amount of insulin consistent with activation of dietary fuel processing system, and since the amount of insulin required to activate a system will vary from patient to patient or even from day to day in the same patient, a rigid length or duration cannot be assigned to the primary series.

After completion of the pre-determined primary insulin pulses—carbohydrate meal/infusion sequence, pulse administration is suspended to allow the "free" insulin concentration to return to the baseline concentration, as shown in Section B of FIG. 1.

When the free insulin concentration is at or near the baseline concentration, a secondary series of smaller insulin pulses is administered to produce a concentration of "free" insulin which oscillates about or near the baseline concentration, as shown by curve J in Section C of FIG. 1 and in FIG. 3. The pulses of insulin of the secondary series are of an amount sufficient to result in peak "free" insulin concentration of 10-300 $\mu$U/ml. The pulses (single or paried) are spaced so as to maintain a relatively constant interpeak "free" insulin concentration of 5 to 15 $\mu$U/ml between discrete pulses or pulse pairs. That is, the effects of one pulse (or pair of pulses) are allowed to dissipate before the next pulse (or pulse pair) is administered.

Administration of this secondary series will (1) together with the primary series, maintain in an active state the body's fuel processing capabilities, in particular the dietary carbohydrate processing system, and (2) permit cycling of hepatic glucose output and hepatic glucose uptake in the period between carbohydrate ingestions or infusions. That is, as the "free" insulin concentration increases above the baseline the glucose-producing function of the activated liver is inhibited and the liver will take up glucose; as the "free" insulin concentration falls towards or below the baseline the activated liver will produce and release glucose.

Once the fuel processing system has been activated and maintained for a period of time (from one to four days) by the primary and secondary series of the insulin infusion program, it is enabled to function in a normal manner. In diabetic patients, repetitive administration of the primary and secondary series over this period enables the liver (and muscle) to function normally to autoregulate body glucose concentrations. While in insulin-dependent diabetic patient a permanent cessation of insulin injections or infusions is not possible, it is anticipated that once the program has been administered for about one to four days the activated dietary fuel processing system would only require a "tune-up" every seven to 30 or more days. Between "tune-ups" the diabetic subject would be returned to a standard conventional therapy (e.g., subcutaneous insulin, oral hypoglycemic agents, diet) in order to maintain basic levels of insulin in the metabolic system. However, with an activated fuel processing system coupled to standard conventional therapy, the diabetic subject would be less subject to wide fluctuations in blodd sugar levels and would need a less restrictive American Diabetes Association diet. Alternatively, the system may be maintained indefinitely by administering the primary series with meals and the secondary series during the nighttime.

An insulin infusion program which conforms to the present invention would involve, for example, administering a primary series of insulin pulses (e.g., intravascularly (including the portal vein), intraperitoneally, or subcutaneously) immediately following the ingestion of a mixed meal containing 10-100 g of dietary carbohydrate of alternatively 10-100 g of glucose or its equivalent (e.g., Sustacal), or the infusion of an equivalent synthetic combination of fuels. The pulses of the primary series, administered every six to thirty minutes over a 6 to 180 minute period, may be of equal or variable amounts with the average amount of the pulses being between 0.01-0.05 Units of insulin per kilogram of body weight (U/kg), and preferably 0.02 to 0.04 U/kg.

As previously stated, it is desired to use the least amount of insulin required to obtain the desired therapeutic effect. These pulses will produce a corresponding series of peaks in the "free" insulin concentration having a peak amplitude of 50-3000 $\mu$U/ml, preferably 100-2000 $\mu$U/ml, in arterial blood or in arterialized venous blood at six to thirty minute intervals. Coincident with these "free" insulin peaks the interpak "free" insulin concentration will increase by 10-500 $\mu$U/ml at siz to thirty minute intervals, achieving a maximum interpeak "free" insulin concentration of 60-1000 $\mu$U/ml at 6 to 180 minutes. Insulin administration is then suspended for an amount of time (e.g., 90-120 minutes) sufficient to allow the "free" insulin concentration to gradually return to the baseline "free" insulin concentration of 5-15 $\mu$U/ml. Following achievement of baseline "free" insulin concentrations, equal or variable insulin pulses of an average amount between 0.001-0.02 U/kg are administered every two to ninety minutes in order to achieve peak "free" insulin concentrations in arterial or arterialized venous blood of 10-300 $\mu$U/ml with a periodicity of two to ninety minutes. This secondary pulse format is continued during the entire period between carbohydrate ingestions or infusions.

The described sequence is repeated with each meal or infusion. The meals are ingested or the infusions are initiated frequently, e.g., from two to eight times a day. Meals and infusions may be administered in any combination, e.g., exclusively meals, exclusively infusions, or meals alternating with infusions in a regular or irregular pattern.

In 8 to 96 hours a significant improvement in the respiratory quotient and carbohydrate oxidation rate should be observed following the ingestion of a carbohydrate-containing meal or an equivalent carbohydrate infusion, observations which are comparable to those seen in normal subjects following ingestion of an equivalent carbohydrate-containing meal or initiation of a comparable infusion.

The primary and secondary series of the described insulin delivery program can be infused using a standard external programmable insulin pump, such as shown schematically in FIG. 4. An external pump configuration would be preferable for use in clinical situations, for example, on an out-patient treatment basis (e.g., for "tune-ups"), for accidentally or surgically traumatized patients, or to bring a patient's metabolic system under microprocessor 12, pump section 14, and infusion catheter 16. Programmable microprocessor 12 includes programming keyboard 18 and display 20, for example an LCD or LED display. Pump section 14 includes pump mechanism 22 and insulin reservoir 24. Infusion catheter 16 extends from pump mechanism 22 and is inserted into the patient to deliver insulin intravascularly (including the portal vein), intraperitoneally, or subcutaneously. For example, in this configuration programmable microprocessor 12 would be programmed (1) to deliver the insulin pulses of the primary series every six to thirty minutes for 6 to 180 minutes, (2) to suspend insulin infusion for 90-120 minutes, and (3) to deliver the smaller insulin pulses of the secondary series until the next primary series is initiated. Initiation of the primary series can be automatically controlled, e.g., programmed to coincide with pre-set carbohydrate infusions, or can be manually controlled, e.g., by pressing the appropriate key on keyboard 18 when a meal is ingested. Alternatively, microprocessor 12 can be programmed to deliver only the primary series (under either manual or automatic control).

Glucose levels can be independently monitored using fingersticks, venipuncture, or glucose sensors. A glucose sensor or analyzer could also be incorporated into the external programmable pump and arranged so as to sound an alarm when glucose levels reach certain pre-set limits as is known in the art, for example, in artificial $\beta$-cells. In this configuration, however, the glucose sensor would not control the initiation or rate of insulin infusion, but would at most be used to suspend insulin infusion if glucose levels reach a pre-set lower limit. Simultaneously with the suspension of insulin infusion, an alarm would alert the patient (or attendant); the insulin infusion program (primary series) could then be manually restarted, if desired, along with the administering of carbohydrates.

The described program can also be administered using a standard implantable programmable insulin pump, such as shown schematically in FIG. 5. The implantable pump configuration would be preferable for long-term self-care by diabetic patients. Referring to FIG. 5, implantable pump assembly 26 includes an external transmitter/receiver unit 28 and the implantable pump unit 30. External transmitter/receiver unit 28 includes programmable microprocessor 32, having programming keyboard 34 and display 36, for example, an LCD or LED display, and telemetry units 38 which transmits control signals received from microprocessor 32 to implantable unit 30 and transmits informational signals received from implantable unit 30 to microprocessor 32. Implantable pump unit 30 includes power supply 40, programmable microprocessor 42, receiver/transmitter 44 which transmits informational signals received from microprocessor 42 to external unit 28 and transmits control signals received from external unit 28 to microprocessor 42, pump mechanism 46, and insulin reservoir 48. Infusion catheter 50 extends from pump mechanism 46 and terminates intravascularly (including the portal vein), intraperitoneally, or subsutaneously. Insulin reservoir 48 can be refilled using syringe 52. Implantable pump unit 30 can be initially programmed to administer the primary and secondary insulin series as described for the external insulin pump configuration. Using external transmitter/receiver unit 28, the insulin delivery pattern can then be initiated and/or changed, for instance, to deliver only the primary series whenever desired.

Glucose levels can be independently monitored as with the external pump configuration using fingersticks, venipucture, or glucose sensors. Glucose sensors may also be incorporated into the implantable insulin pump and arranged so as to trasmit glucose levels to the external unit 28, as is well known in the art. The external unit could merely sound an alarm when glucose levels reach a pre-settable limit, or could be programmed to suspend insulin infusion (as with the external pump configuration) and sound an alarm simultaneously. It is important to note that in both the external and implantable configurations, the glucose-level-triggered alarm is used primarily for informational purposes and would not independently initiate insulin or glucose infusions.

It should also be noted that administering carbohydrates so as to induce elevational levels sufficient to work in combination with the described insulin-infusion pattern runs directly contrary to standard treatment regimens for diabetic patients. Further, although the pulses are timed to coincide wih the anticipated elevated portal vein glucose concentration following the ingestion of carbohydrate-containing meals or following the initiation of carbohydrate infusions, the pattern of insulin infusion and the resulting insulin concentrations of the present invention differ significantly from those which occur in normal man and from those which occur in diabetic patients on a typical treatment program.

The program of insulin infusion described can be used in diabetic subjects for rapid and efficient primary activation of the fuel processing system, in particular, the dietary carbohydrate processing system, or, for maintenance of the system by the administration, immediately prior to or following the ingestion of meals, of defined intravenous pulses of insulin of smaller magnitude than that used for primary activation. This insulin delivery pattern could also be effective in preserving and/or restoring fuel (e.g., glucose, amino acids, lipids) processing capabilities of hepatic and other tissues (e.g., muscle) in both diabetic and non-diabetic subjects in acute care situations, i.e., traumatized individuals (surgical patients, accident victims) or patients on hyperalimentation.

Other embodiments are within the following claims. For example, the interprandial (including night-time) "free" insulin concentration may be maintained at or near the baseline level by substituting standard insulin therapy for the secondary series, for example, using long-acting (NPH) insulin or using continuous low-level insulin infusion, administering the primary series of pulses with meals; and the priamry and/or secondary series could be administered intravenously (including the portal vein), intraperitoneally, or subcutaneously by using multiple oscillatory insulin injection regimens.

I claim:

1. A method for treating a human subject having predetermined body tissues characterized by abnormal or impaired dietary fuel processing capability, comprising:

(a) administering carbohydrate to said subject to produce in the blood supply to said body tissues a substantially elevated carbohydrate concentration during a time period following such administration; and (b) infusing insulin into said subject during at least a portion of said time period in a prearranged series of pulses separated by prearranged time periods, thereby producing in the blood supply to said body tissues a series of peaks in the free insulin concentration, said prearranged time periods selected to produce successively increasing free insulin concentration minima between said peaks.

2. The method of claim 1, wherein step (b) is carried out during a first prearranged time period, and said method further comprises:

(c) infusing insulin into said subject during a second time period in a series of pulses of lesser magnitude than the pulses during said first time period to produce oscillations in the free insulin concentration in the blood supply to said body tissues, said second time period being delayed from said first time period by an amount of time such that said free insulin concentration has returned to a baseline level.

3. A method for treating a human subject having predetermined body tissues with abnormal or impaired dietary fuel processing capability to produce a functional improvement in such dietary fuel processing capability, comprising:

(a) infusing a first pulse of insulin into said subject at a prearranged time period following ingestion of a normal to high carbohydrate concentration meal to produce in the blood supply to said body tissues a rapid increase in the free insulin concentration coinciding with an elevated carbohydrate concentration but independent of the magnitude of said carbohydrate concentration; and (b) infusing a prearranged series of additional pulses of insulin into said subject, each of said additional pulses being spaced in time relative to said first pulse and to each other to produce a series of peaks in said free insulin concentration in said blood supply with successively increasing free insulin concentration minima between peaks.

4. The method of claim 1 wherein said pulses of step (b) are administered over a period of up to three hours.

5. The method of claim 1 wherein said pulses of step (b) are administered over a period of 6 to 180 minutes.

6. The method of claim 2 wherein said pulses of step (c) are arranged to produce oscillation in said free insulin concentration about a baseline concentration and thereby maintain the dietary carbohydrate processing capabilities of said subject's body tissues in an active state.

7. The method of claim 2 wherein step (c) is continued until step (a) is repeated.

8. The method of any of claims 1, 2, 3, 4, 5, 6, or 7 wherein steps (a) and (b) are coincident.

9. The method of any of claims 1, 2, 3, 4, 5, 6, or 7 wherein said activating step is performed from 2 to 8 times a day.

10. The method of any of claims 1, 2, 3, 4, 5, 6, or 7 wherein step (a) is performed by ingesting carbohydrates.

11. The method of any of claims 1, 2, 3, 4, 5, 6, or 7 wherein step (a) is performed by infusing carbohydrate into said subject's bloodstream.

12. The method of any of claims 1, 2, 3, 4, 5, 6, or 7 wherein step (a) is performed by administering from 10-100 g of dietary carbohydrate.

13. The method of any of claim 1, 4, or 5 wherein said pulses each fall within the range of about 0.01-0.05 U/kg.

14. The method of any of claims 1, 4, or 5 wherein said pulses each fall within the range of about 0.02-0.04 U/kg.

15. The method of any of claims 1, 4, or 5 wherein said pulses are administered every six to thirty minutes.

16. The method of any of claims 2, 6, or 7 wherein said pulses of step (c) each fall within the range of about 0.001-0.02 U/kg.

17. The method of any of claims 2, 6, or 7 wherein said pulses of step (c) are administered every two to ninety minutes.

18. The method of claim 1 wherein said pulses are on the average within the range of about 0.01-0.05 U/kg.

19. The method of claim 1 wherein said pulses are on the average within the range of about 0.02-0.04 U/kg.

20. The method of claim 1 wherein said pulses are administered every six to thirty minutes.

21. The method of claim 2 wherein said pulses of step (b) are each within the ragne of about 0.01-0.05 U/kg; said pulses of step (c) are each within the range of about 0.001-0.02 U/kg; said pulses of step (b) are administered every six to thirty minutes; said pulses of step (c) are administered every two to ninety minutes; step (a) is performed from two to eight times a day by administering 10-100 g of dietary carbohydrate; and step (b) is performed in coincident manner with step (a).

* * * * *